United States Patent
Jang et al.

(10) Patent No.: US 11,623,000 B2
(45) Date of Patent: Apr. 11, 2023

(54) PHARMACEUTICAL COMPOSITION FOR TREATING FOOT PAIN DISEASE INCLUDING BOTULINUM TOXIN AND HYALURONIC ACID, AND FOOT PAIN DISEASE TREATMENT METHOD USING SAME

(71) Applicant: ATGC CO., LTD., Seoul (KR)

(72) Inventors: Sung Su Jang, Seoul (KR); Haksup Lee, Seongnam-si (KR); Yongshik Ahn, Seoul (KR); Jonghyo Kim, Seoul (KR); Seungjin Shin, Seongnam-si (KR)

(73) Assignee: ATGC CO., LTD., Seoul (KR)

( * ) Notice: Subject to any disclaimer, the term of this patent is extended or adjusted under 35 U.S.C. 154(b) by 429 days.

(21) Appl. No.: 16/615,494

(22) PCT Filed: May 21, 2018

(86) PCT No.: PCT/KR2018/005758
§ 371 (c)(1),
(2) Date: Nov. 21, 2019

(87) PCT Pub. No.: WO2018/216974
PCT Pub. Date: Nov. 29, 2018

(65) Prior Publication Data
US 2020/0085924 A1 Mar. 19, 2020

Related U.S. Application Data

(60) Provisional application No. 62/510,455, filed on May 24, 2017.

(51) Int. Cl.
*A61K 38/48* (2006.01)
*A61K 31/728* (2006.01)

(52) U.S. Cl.
CPC ........ *A61K 38/4893* (2013.01); *A61K 31/728* (2013.01)

(58) Field of Classification Search
None
See application file for complete search history.

(56) References Cited

U.S. PATENT DOCUMENTS

2010/0172940 A1* 7/2010 Petrella .................. A61P 19/04
424/239.1

FOREIGN PATENT DOCUMENTS

| KR | 10-2003-0009431 A | 1/2003 |
| KR | 10-2005-0109969 A | 11/2005 |
| WO | 2010078648 A1 | 7/2010 |

OTHER PUBLICATIONS

Kenner, Cosmetic Dermatology 24(6): 270-276 (2011).*
(Continued)

*Primary Examiner* — Erin M. Bowers
(74) *Attorney, Agent, or Firm* — Riverside Law LLP

(57) ABSTRACT

The present invention relates to a pharmaceutical composition for treating a foot pain disease, including botulinum toxin and hyaluronic acid, and a foot pain disease treatment method using the same. More specifically, the composition according to the present invention can exhibit a synergistic action of increasing both anti-inflammatory and anti-pain activity through an inflammation-inhibiting effect on a foot pain disease such as pain arising from plantar fasciitis, foot fasciitis, Achilles tendon damage, flat feet, diabetes, and gout. Thus, the composition according to the present invention is expected to be able to be usefully used subcutaneously in the foot as a liquid injection agent that exhibits an effect of treating or alleviating a foot pain disease.

9 Claims, 1 Drawing Sheet

Negative control vs. Other groups, *: p<0.05, ***:p<0.001

(56) References Cited

OTHER PUBLICATIONS

Huang et al., J. Rehabil. Med. 42: 136-140 (2010).*
Kumai et al., J. Orthop. Sci. 19: 603-611 (2014).*
1. Kumai, T. et al., "The short-term effect after a single injection of high-molecular-weight hyaluronic acid in patients with enthesopathies (lateral epicondylitis, patellar tendinopathy, insertional Achilles tendinopathy, and plantar fasciitis): a preliminary study", Journal of Orthopaedic Science, 2014, vol. 19(4), pp. 603-611.
2. Huang, Y.-C. et al., "Ultrasonographic guided botulinum toxin type A for plantar fasciitis: an outcome-based investigation for treating pain and gait changes", Journal of Rehabilitation Medicine, 2010, vol. 42(2), pp. 136-140.
3. Elizondo-Rodriguez, J. et al., "A comparison of botulinum toxin a and intralesional steroids for the treatment of plantar fasciitis: a randomized, double-blinded study", Foot & Ankle International, 2013, vol. 34(1), pp. 8-14.

* cited by examiner

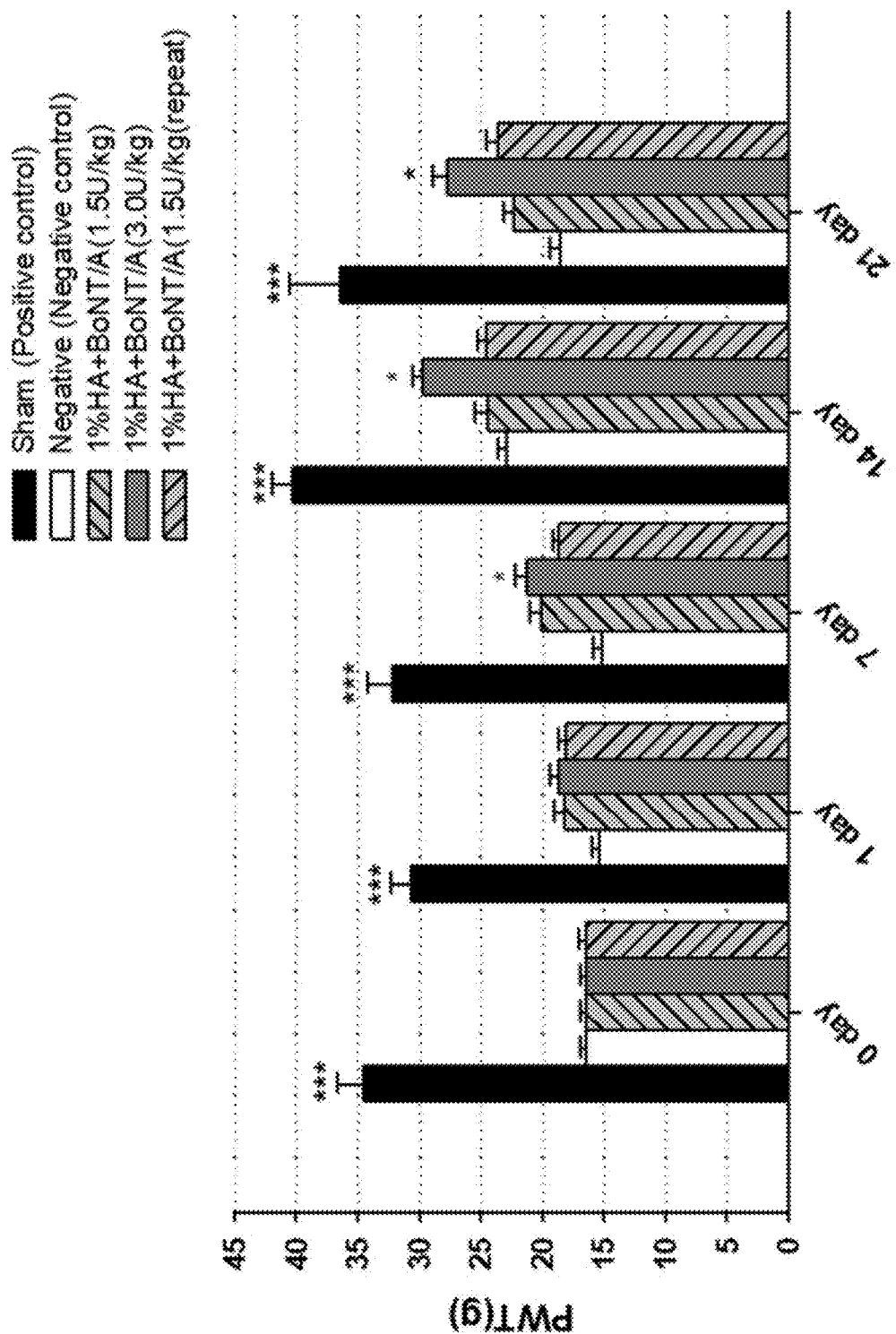

PHARMACEUTICAL COMPOSITION FOR TREATING FOOT PAIN DISEASE INCLUDING BOTULINUM TOXIN AND HYALURONIC ACID, AND FOOT PAIN DISEASE TREATMENT METHOD USING SAME

CROSS-REFERENCE TO RELATED APPLICATIONS

This application is the U.S. national phase application filed under 35 U.S.C. § 371 claiming benefit to International Patent Application No. PCT/KR2018/005758, filed on May 21, 2018, which claims priority to U.S. provisional application no. 62/510,455, filed May 24, 2017, the disclosures of which are incorporated herein by reference in their entirety.

TECHNICAL FIELD

The present invention relates a pharmaceutical composition for treating a foot pain disease, including botulinum toxin and hyaluronic acid, and a foot pain disease treatment method using the same.

BACKGROUND ART

Botulinum toxin is a neurotoxin produced by a Gram-positive anaerobic bacterium, *Clostridium botulinum*. Botulinum toxin is classified into eight neurotoxins, and among them, seven (A, B, C, D, E, F, and G) may cause nerve paralysis. Among them, the most deadly botulinum toxin known as a natural biological agent is type A, the toxin protein has a size of 150 kDa and binds to a non-toxin protein to form a complex, and the size of the complex is up to 900 kDa depending on the type of neurotoxin.

Botulinum toxin has an effect of causing temporary paralysis of muscle, and causes local muscular paralysis according to a mechanism of inhibiting the secretion of acetylcholine at the myoneural junction of a motor nerve terminal (binding to the cholinergic terminal to enter the nerve cells). Botulinum toxin has an effect of inhibiting pain such as chronic myofascial pain by local muscle paralysis, low back pain, muscular stiffness, and tension type headaches, and inhibits pain by inhibiting acetylcholine to block nerve signaling.

Botulinum toxin was approved by the US FDA in 1989, and has been used for the purpose of alleviating strabismus and glabellar wrinkles. Botulinum toxin has been used for treating strabismus, facial spasms, blepharospasm, myotonia, and the like, and has been used for cosmetic purposes such as removal of wrinkles and square jaw surgery.

The duration time of botulinum toxin injected into muscle and skin tissues is within 3 to 6 months, the injection effect begins within 3 days, and the maximum effect appears within 1 to 2 weeks. When signaling is blocked by inhibiting the secretion of acetylcholine at the myoneural junction by botulinum toxin, a new nerve branch is created to reduce the nerve paralysis effect by botulinum toxin, and thus, botulinum toxin needs to be administered periodically.

Botulinum toxin may cause side effects such as headaches, ptosis, dysphagia, and xerostomia, but there is no direct death from the botulinum toxin, and it is known that when botulinum toxin is used at an appropriate dose, there is no problem with safety. However, the application thereof is limited for pregnant women or breastfeeding women.

Foot pain is a disease in which inflammation occurs and is accompanied by a pain in a specific part of the foot, and examples thereof include plantar fasciitis, foot fasciitis, diabetic foot nerve pain, a foot pain disease by gout, and the like.

Among them, plantar fasciitis as a representative disease is a disease in which inflammation occurs in a tissue called the plantar fascia, located on the sole of the foot, and pain is caused. The plantar fascia is a stiff fibrous tissue that widely spreads on the sole of the foot, starts under the five toes and gathers into one tendon, and then is attached to the anteromedial area of the heel bone, and plays an important role in maintaining the arch of the foot when one is standing or walking, and when the plantar fascia is injured, inflammation and pain may be caused. Accordingly, as the cause thereof, inflammation occurs due to the stimulation by stress at an area in which the plantar fascia is attached to the calcaneus, and pain sometimes occurs due to the stimulation of surrounding nerves. In most cases, ultrasonography is often used to diagnose plantar fasciitis, and it can be seen how thick the plantar fascia is by observing the area in which the plantar fascia is attached to the calcaneus. Further, when there is inflammation, a thick fascia can be found along with a low reflex of the plantar fascia.

The purpose of treating plantar fasciitis is to reduce pain, maintain mobility, and minimize the disorder. Examples of a treatment method thereof include a non-drug (adjustment of quantity of exercise and method, stretching exercises, muscular force strengthening exercises, wearing an aid, and adjustment of shoes) treatment and a drug (non-steroidal anti-inflammatory analgesic, steroid injection, extracorporeal shock wave treatment, and surgical treatment) treatment. Since the inflammation and pain due to the plantar fascia is a disease that causes many limitations in daily life, there are side effects such as hepatotoxicity, renal failure, peptic ulcers, and gastrointestinal hemorrhaging when the drug is taken for a long period of time, and thus there is an urgent need for a treatment method without any side effects instead of improvement effects which depend on the drug.

In order to relieve the inflammation and pain of plantar fasciitis, there is a report in which pain is relieved by administering botulinum toxin alone to relieve inflammation. Further, there is a clinical study in which the effects are improved compared to steroidal preparations, when plantar fasciitis is treated by botulinum toxin. In addition, there is a report in which an anti-inflammatory effect is exhibited by using hyaluronic acid to inhibit IL-1 beta which is a main cytokine of inflammation.

In the early stage of plantar fasciitis, symptoms can be relieved using a non-drug treatment, but a chronic disease accompanied by inflammation and pain should be treated by a drug treatment and a plantar subcutaneous injection therapy. Since there is no product which has been approved and commercially available as a medicine for preventing and treating a foot pain disease, such as pain caused by plantar fasciitis, foot fasciitis, diabetic foot nerve pain, and a foot pain disease by gout, using a mixed composition of botulinum toxin and hyaluronic acid to date, there is a need for a plantar subcutaneous injectable preparation in which botulinum toxin and hyaluronic acid are mixed.

DISCLOSURE

Technical Problem

The present invention has been contrived to solve the above-mentioned problems, and the present inventors have made intensive efforts to find an injectable preparation capable of relieving inflammation and pain due to chronic plantar fasciitis and maintaining the functionality thereof, and as a result, confirmed that a botulinum toxin and hyaluronic acid complex preparation of the present invention had an effect of relieving inflammation and pain due to plantar fasciitis, thereby completing the present invention.

Thus, an object of the present invention is to provide a pharmaceutical composition for treating a foot pain disease, including hyaluronic acid or a pharmaceutically acceptable salt thereof, and botulinum toxin.

Another object of the present invention is to provide a method for treating foot pain, the method including a step of administering, to a subject, a pharmaceutical composition for treating a foot pain disease, including the composition or a pharmaceutically acceptable salt thereof.

Still another object of the present invention is to provide a use of the pharmaceutical composition for treating a foot pain disease for the production of a therapeutic agent for foot pain.

However, a technical problem to be solved by the present invention is not limited to the aforementioned problems, and other problems that are not mentioned may be clearly understood by those skilled in the art from the following description.

Technical Solution

In order to achieve the objects of the present invention as described above, the present invention provides a pharmaceutical composition for treating a foot pain disease, including hyaluronic acid or a pharmaceutically acceptable salt thereof, and botulinum toxin.

As an embodiment of the present invention, the botulinum toxin may be type A, B, C, D, E, F, or G, preferably type A.

As another embodiment of the present invention, the botulinum toxin may be included at 0.01 to 250 units (U), preferably 0.01 to 20 units (U).

As still another embodiment of the present invention, the botulinum toxin may be a toxin protein or a complex protein.

As yet another embodiment of the present invention, the hyaluronic acid may have a molecular weight of 1,000 KDa or less.

As yet another embodiment of the present invention, the hyaluronic acid may be included in an amount of 0.5 wt % to 5 wt %, preferably 0.5 wt % to 1 wt %.

As a further embodiment of the present invention, the foot pain may be caused from one or more selected from the group consisting of plantar fasciitis, foot fasciitis, diabetes, and gout. Furthermore, the present invention provides a method for treating a foot pain disease, the method including a step of administering the pharmaceutical composition to a subject.

As an embodiment of the present invention, the administration may be administration subcutaneously into a foot area.

As another embodiment of the present invention, the botulinum toxin may be type A, B, C, D, E, F, or G, preferably type A.

Further, the present invention provides a use of the composition for the production of a therapeutic agent for a foot pain disease.

As an embodiment of the present invention, the therapeutic agent may be a liquid.

Advantageous Effects

The present invention relates to a composition for treating a foot pain disease, including botulinum toxin and hyaluronic acid. More specifically, the composition according to the present invention can exhibit a synergistic action of increasing both anti-inflammatory and anti-pain activity through an inflammation-inhibiting effect on a foot pain disease such as pain arise from plantar fasciitis, foot fasciitis, Achilles tendon damage, flat feet, diabetes, and gout. Thus, the composition according to the present invention is expected to be able to be usefully used subcutaneously in the sole of a foot as a liquid injection agent that exhibits an effect of treating or alleviating a foot pain disease.

DESCRIPTION OF DRAWINGS

FIG. 1 is a view illustrating the degree of pain reduction of the composition of the present invention through a Von Frey test.

MODES OF THE INVENTION

The present inventors specifically confirmed that a botulinum toxin and hyaluronic acid complex preparation of the present invention could relieve the inflammation and pain of a foot pain disease and maintain the functionality thereof, thereby completing the present invention based on this.

Hereinafter, the present invention will be described in detail.

The present invention provides a pharmaceutical composition for treating a foot pain disease, including botulinum toxin or a pharmaceutically acceptable salt thereof, and hyaluronic acid or a pharmaceutically acceptable salt thereof.

The pharmaceutical composition according to the present invention may be a liquid, and may be preferably formulated into an injection dosage form. Further, the composition may be administered subcutaneously into a foot area in order to treat foot pain, and is preferably administered subcutaneously into the sole of a foot in order to treat plantar fasciitis, but is not limited thereto.

As used herein, the term "botulinum toxin" refers to a type of botulinum toxin that may be produced by bacteria or produced by a recombinant technique, but includes any known type of botulinum toxin, and a modified variant or a fused protein thereof, and any type of botulinum toxin that may be subsequently discovered. The botulinum toxin is classified into eight neurotoxins, and seven botulinum toxin serotypes A, B, C, D, E, F, and G may cause nerve paralysis. This protein is classified into a protein that includes a complex and a protein that does not include a complex, and a pure toxin protein has a molecular weight of 150 KDa, and various proteins with 300 KDa, 500 KDa, and 900 KDa are produced according to whether the complex is formed.

The botulinum toxin used in the composition of the present invention may be alternatively a botulinum toxin derivative, that is, a compound that has botulinum toxin activity, but includes one or more chemical modifications or functional modifications as compared to natural or recombinant prototype botulinum toxin. For example, the botulinum toxin may be a modified neurotoxin (for example, a neurotoxin having one or more amino acid deletions, modifications, or substitutions as compared to a prototype neurotoxin or neurotoxin produced by recombination, derivatives thereof, or fragments thereof). For example, the botulinum toxin may be a botulinum toxin that strengthens characteristics thereof or reduces undesirable side effects thereof, but is modified in a way in which the preferable botulinum toxin activity is still retained. Alternatively, the botulinum toxin may be a toxin produced using a recombinant or synthetic chemical technique (for example, a recombinant peptide, a fusion protein, or a hybrid neurotoxin, prepared from different botulinum toxin serotype subunits or domains (see, for example, U.S. Pat. No. 6,444,209)). The botulinum toxin may also be a part of the whole molecule that has been proven to have the required botulinum toxin activity, and may be used as is or a part of a combination or conjugate molecule, for example, a fusion protein in such a case. Further, the botulinum toxin may be in the form of a precursor for botulinum toxin, which may itself be non-toxic, for example, a non-toxic zinc protease that may become toxic when decomposed by protein hydrolysis.

As used herein, the "hyaluronic acid" is one of complex polysaccharides including an amino acid and uronic acid, and has a low molecular weight (500 KDa to 1,000 KDa), which is the same size as that of hyaluronic acid present in the human body, and thus, is not only biologically safe, but also more effective than a high-molecular weight hyaluronic acid in a decrease in the inflammation level of synovial fluid and a rheological recovery during the subcutaneous injection. On the other hand, high-molecular weight hyaluronic acid (2,300 KDa or more) has an advantage in that the administration frequency may be reduced due to high viscoelasticity.

As used herein, the "pharmaceutically acceptable salt of hyaluronic acid" and the "pharmaceutically acceptable salt of botulinum toxin" refer to salts that are recognized to be generally used for an animal, particularly, a human, and examples of a salt used to produce a base addition salt include an inorganic salt such as a lithium, sodium, potassium, calcium, magnesium, or aluminum salt, or an organic salt such as ethylamine, diethylamine, ethylene diamine, ethanolamine, diethanolamine, arginine, lysine, histidine, or piperazine; or examples of an acid addition salt include organic salts such as acetates, citrates, lactates, malonates, maleates, tartarates, fumarates, benzoates, aspartates, glutamates, succinates, oleates, trifluoroacetates, oxalates, pamoates, or gluconates, inorganic salts such as a chlorides, sulfates, borates, or carbonates, and the like, but the examples are not limited thereto. Under the assumption that the salt is pharmaceutically acceptable, the characteristics of the salt are not important factors. The pharmaceutically acceptable salt of the composition of the present invention may be obtained by a typical method well known in the art.

The pharmaceutical composition of the present invention may include a pharmaceutically acceptable carrier in addition to an active ingredient. In this case, the pharmaceutically acceptable carrier is typically used during formulation, and includes lactose, dextrose, sucrose, sorbitol, mannitol, starch, gum acacia, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, but is not limited thereto. Furthermore, the pharmaceutically acceptable carrier may further include a lubricant, a wetting agent, a sweetening agent, a flavoring agent, an emulsifier, a suspending agent, a preservative, and the like, in addition to the aforementioned ingredients.

The pharmaceutical composition of the present invention is administered in a pharmaceutically effective amount. In the present invention, "the pharmaceutically effective amount" refers to an amount sufficient to treat a disease at a reasonable benefit/risk ratio applicable to medical treatment, and the level of the effective dosage can be determined according to the type and severity of disease of a patient, the activity of the drug, the drug sensitivity in a patient, the administration time, the administration pathway and release rate, the treatment duration, factors including drugs that are simultaneously used with the composition of the present invention, or other factors well-known in the medical field. The pharmaceutical composition according to the present invention may be administered as single therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

The "plantar fasciitis" which is a disease to be treated in the present invention collectively refers to a disease in which pain occurs due to repetitive stress on the fascia which is connected from the heel to the toe, and severe pain occurs when the feet step on the ground, and may include a foot pain disease such as pain caused by foot fasciitis, pain caused by Achilles tendon damage, pain caused by flat feet, diabetic foot nerve pain, and pain caused by gout, but is not limited thereto.

Meanwhile, another aspect of the present invention provides a method for treating plantar fasciitis, the method including a step of administering the composition to a subject.

In the present invention, "a subject" refers to a subject in need of treatment of a disease, and more specifically, refers to a mammal such as a human or a non-human primate, a mouse, a rat, a dog, a cat, a horse, and a cow.

The "local administration" applied to the present invention refers to a direct administration of a drug into or near an area in or on the body of an animal in need of a biological effect of the medicine. The local administration excludes an administration of a systemic route such as intravenous administration or oral administration. The topical administration is included in the form of a local administration in which the pharmaceutical formation is administered subcutaneously into the sole of a foot of a person. For the administration, it is preferred that a composition in a form in which the active ingredient botulinum toxin and a hyaluronic acid ingredient are mixed may be administered by plantar subcutaneous injection, and the treatment is sufficient with repeated administrations once or twice every three months.

The active ingredient dosage of the composition according to the present invention varies depending on various factors such as the age of a patient, the degree of pain, and the time of onset. Based on the active ingredient based on the botulinum toxin type A, about 0.01 to about 250 units (U), preferably about 0.01 to 100 units (U), more preferably 0.01 to 50 units (U), and even more preferably 0.01 to 20 units (U) of the botulinum toxin may be administered. The dosage may be appropriately selected by those skilled in the art depending on the condition and body weight of a patient, the severity of the disease, the drug form, the administration route, and the time.

The hyaluronic ingredient according to the present invention may be administered in an amount of about 0.5 wt % to about 5 wt %, preferably about 0.5 wt % to about 3 wt %, and more preferably about 0.5 wt % to about 1 wt %.

For the administration, a pharmaceutical composition obtained by mixing the active ingredient botulinum toxin with the hyaluronic acid ingredient is injected subcutaneously into the sole of a foot, and the treatment is sufficient with repeated administrations once to twice every three months.

In the method, hyaluronic acid may serve to relieve pain and treat inflammation by performing a lubrication action and a buffering action in the subcutaneous sole of a foot, and botulinum toxin will be able to facilitate functionality by inhibiting acetylcholine to block the neuron signaling of pain and relieve pain. Since the use of an oral drug may be reduced using the composition of the present invention, the human side effects of the oral drug may be consequently reduced.

In the present invention, botulinum toxin and hyaluronic acid may be administered subcutaneously into the sole of a foot in the form of a mixture of the pharmaceutical composition.

The composition according to the present invention may be used for the use of producing a therapeutic agent for foot pain, and in this case, the therapeutic agent may be preferably a liquid, and more preferably a liquid injection.

Hereinafter, preferred examples for helping the understanding of the present invention will be suggested. However, the following examples are provided only to more easily understand the present invention, and the contents of the present invention are not limited by the following examples.

EXAMPLE 1

Experimental Preparation and Experimental Methods 1-1. Production of Experimental Material Hyaluronic acid (HA) was dissolved in a 50 mM sodium phosphate buffer (pH 6.8) so as to obtain a concentration of 10 mg/ml. After the body weight of an animal was measured on the day of administration, botulinum toxin type A (BoNT/A) was respectively put into the prepared hyaluronic acid based on the average body weight of a test group, such that the final administration amount of the botulinum toxin type A (BoNT/A) was 1.5 U/kg and 3.0 U/kg, and the resulting mixture was stirred and mixed for 30 minutes.

1-2. Animal Model

For an animal model of the present experiment, the model was induced by administering 100 µl (1 mg/mL) of a complete Freund's adjuvant (FCA) to the right hind paw sole of a Sprague-Dawley (SD) white rat via a subcutaneous route. For group construction, a total of 5 groups of a naïve sham in which the model was not induced, a negative control in which the model was induced, and then 50 µl of a 50 mM sodium phosphate buffer (pH 6.8) was administered, a test group (1% HA+1.5 U/kg BoNT/A) in which the model was induced, and then 50 µl of HA+BoNT/A (0.5 mg of 1% HA, 0.454 Unit of BoNT/A (based on 300 g of the animal body weight)) was administered once, a test group (1% HA+3.0 U/kg BoNT/A) in which 50 µl of HA+BoNT/A (0.5 mg of 1% HA, 0.909 Unit of BoNT/A (based on 300 g of the animal body weight)) was administered once, and a test group (1% HA+1.5 U/kg BoNT/A) in which 50 µl of HA+BoNT/A (0.5 mg of 1% HA, 0.454 Unit of BoNT/A (based on 300 g of the animal body weight)) was administered twice at a weekly interval were produced, and a test material was administered subcutaneously into the right hind paw soles of 5 animals belonging to the naïve sham and 10 animals per the negative control and the test groups.

Before the test material was administered subcutaneously into the sole of a foot, on the day after the complete Freund's adjuvant (FCA) was administered, measurements were performed three times using a paw withdrawal threshold (PWT) test in order to evaluate the confirmation of the model induction and the degree of induction, and a group separation was performed using the measured values. After the group separation, about 50 µl of the test material was administered to the right hind paw sole where inflammation was caused, the animals were observed for 21 days, and after the complete Freund's adjuvant (FCA) was administered only to the test group, the PWT test was performed on day 7, and then a secondary administration was performed.

1-3. Paw Withdrawal Threshold (PWT) Test

In order to confirm the treatment efficacy of plantar fasciitis in the example using the FCA induction model, a PWT test as a parameter for measuring pain was performed.

For the PWT test, an effect of inhibiting acute pain was measured by applying physical stimulation through a Von Frey filament using a dynamic plantar aesthesiometer (UGO BASILE 37450, Italy). One animal each was put into one compartment of an acrylic cage, and was left to stand for 15 minutes, such that the rat could acclimate to a new environment. After acclimation to the environment, an aesthesiometer was set at 0 to 50 g and 0 to 20 sec, and as a method for measuring an allodynia stimulated by a stimulator, a hind paw withdraw threshold (force at the moment when the experimental body evades the stimulator: grams) of a withdrawal response of the feet was measured three times at 5-minute intervals by stimulating the affected side plantar area at a strength from 0 g to 50 g. The PWT test was measured on day 1, 2, 7, 14, and 21 after the administration of FCA.

EXAMPLE 2

Confirmation of Effects of Botulinum Toxin and Hyaluronic Acid Complex Preparation on Inhibition of Foot Area Pain in FCA-Induced Foot Aarea Hyperalgesia Model FCA is a material that induces pain by causing an inflammation response when administered to the hind paw plantar sole via a subcutaneous route, has been widely used to study pain and evaluate efficacy in a FCA-induced animal model, and is suitable particularly for the evaluation of the degree of a foot pain disease such as plantar fasciitis by causing inflammation in the plantar fascia. Thus, in order to confirm the effects of HA+BoNT/A on the treatment of foot pain using the FCA-induced model, a Von Frey test as a parameter for measuring pain was tested by the method in Example 1.

2-1 Von Frey Test

In order to evaluate the confirmation and degree of model induction after the administration of FCA, the Von Frey test was performed by the method in Example 1-3, and in this case, the higher the numerical values on the graph is, the better the effect of reducing pain is exhibited.

The data in FIG. 1 was shown as a mean±standard deviation (sd), and for statistical analysis, the least significant difference (LSD) was used as SPSS one-way ANOVA analysis and post hoc analysis. As a result, as illustrated in FIG. 1, on day 0 after administration, it could be confirmed that both the test group (HA+BoNT/A group) and the negative control (FCA-induced group) showed a significant difference with the positive control (sham group), and thus, it could be seen that the model was induced, and the groups were separated by making the pain evaluation average numerical values equal. Further, as a result of the Von Frey test performed on day 7, 14, and 21 after administration, when the test group (1% HA+3.0 U/kg BoNT/A) in which the model was induced, and then 50 μl of HA+BoN/TA (0.5 mg of 1% HA, 0.909 Unit of BoNT/A (based on 300 g of the animal body weight) was administered once was compared with the negative control in which the model was induced, and then 50 μl of a 50 mM sodium phosphate buffer (pH 6.8) was administered, a tendency to statistically significantly decrease the pain measurement numerical values was exhibited, and a tendency, which was not statistically significant, to increase the pain measurement average value according to the concentration of HA+BoNT/A was exhibited.

Based on the results, it was confirmed that during the subcutaneous administration to the hind paw sole, the HA+BoNT/A group had an effect of inhibiting pain.

Therefore, when botulinum toxin and hyaluronic acid were simultaneously used, the simultaneous use exhibits an effect on anti-pain action, and thus, is expected to be able to be usefully used for alleviating pain in the foot area.

The above-described description of the present invention is provided for illustrative purposes, and a person skilled in the art to which the present invention pertains will understand that the present invention can be easily modified into other specific forms without changing the technical spirit or essential features of the present invention. Therefore, it should be understood that the above-described examples are only exemplary in all aspects and are not restrictive.

INDUSTRIAL APPLICABILITY

The present invention relates to a composition for treating a foot pain disease, including botulinum toxin and hyaluronic acid, and the composition of the present invention is expected to be able to be usefully used subcutaneously in the sole of a foot as a liquid injection agent that exhibits an effect of treating or alleviating a foot pain disease such as pain arising from plantar fasciitis, foot fasciitis, Achilles tendon damage, flat feet, diabetes, and gout.

What is claimed is:

1. A method for treating foot pain in a subject comprising administering to a subject in need thereof, a pharmaceutical composition comprising hyaluronic acid or a pharmaceutically acceptable salt thereof, and botulinum toxin,
   wherein the pharmaceutical composition reduces inflammation and pain of foot pain, and
   wherein the foot pain arises from diabetes or gout.
2. The method of claim 1, wherein the administration is a subcutaneous administration to the foot area.
3. The method of claim 1, wherein the botulinum toxin is comprised at 0.01 to 250 units (U).
4. The method of claim 1, wherein a type of the botulinum toxin is any one selected from the group consisting of A, B, C, D, E, F, and G.
5. The method of claim 1, wherein the botulinum toxin is comprised at 0.01 to 20 units (U).
6. The method of claim 1, wherein the botulinum toxin is a toxin protein or a complex protein.
7. The method of claim 1, wherein the hyaluronic acid has a molecular weight of 1,000 kDa or less.
8. The method of claim 1, wherein the hyaluronic acid is comprised in an amount of 0.5 wt % to 5 wt %.
9. The method of claim 1, wherein the hyaluronic acid is comprised in an amount of 0.5 wt % to 1 wt %.

* * * * *